United States Patent [19]
Camden

[11] Patent Number: 5,908,855
[45] Date of Patent: *Jun. 1, 1999

[54] COMPOSITIONS FOR TREATING VIRAL INFECTIONS

[75] Inventor: James Berger Camden, West Chester, Ohio

[73] Assignee: The Procter & Gamble Company, Cincinati, Ohio

[ * ] Notice: Under 35 U.S.C. 154(b), the term of this patent shall be extended for 1128 days.

[21] Appl. No.: 08/674,180

[22] Filed: Jul. 16, 1996

[51] Int. Cl.⁶ .......................... A61K 31/41; A61K 31/415
[52] U.S. Cl. ............................................. 514/383; 514/394
[58] Field of Search ...................... 514/394, 383

[56] References Cited

U.S. PATENT DOCUMENTS

| | | | |
|---|---|---|---|
| 4,079,062 | 3/1978 | Van Reet et al. | 260/8 |
| 4,160,838 | 7/1979 | Van Reet et al. | 424/269 |
| 4,404,216 | 9/1983 | Richardson | 514/383 |
| 4,490,540 | 12/1984 | Heeres | 548/336 |
| 5,114,951 | 5/1992 | King | 514/290 |
| 5,126,359 | 6/1992 | Stroeck et al. | 514/383 |
| 5,211,736 | 5/1993 | Lai | 504/275 |
| 5,360,612 | 11/1994 | Fries et al. | 514/383 |
| 5,565,478 | 10/1996 | Kohn et al. | 514/359 |
| 5,664,751 | 9/1997 | Camden | 514/383 |

FOREIGN PATENT DOCUMENTS

| | | |
|---|---|---|
| 44605 | 1/1982 | European Pat. Off. . |
| 196855 | 10/1986 | European Pat. Off. . |
| 2078719 | 1/1982 | United Kingdom . |
| WO96/40119 | 12/1996 | WIPO . |

OTHER PUBLICATIONS

Physicians Desk Reference, 15:35:33, Diflucan, Medical Economics Data Production Co, Montvale, NJ (1995).
Benzaquen et al, Nature Medicine, 1, (6), Jun., 1995.
Schwartz et al. "Inhibition of all trans–retinoic acid metabolism by Fluconazole in vitro and in Patients with Acute Promyelocytic Leukemia", Biochem. Pharmacol., vol. 50, No. 7, pp. 923–928, (Sep. 1995).
The Merck Index, 12th ed., Merck & Co, (1996) 4158 and 10252.
The Merck Index, 1989, 11th ed, Merck & Co., Rahway, NJ. p. 1232.
Sahai et al, J of Infectious Diseases 169 (5) 1994 pp. 1103–1107 (abstract only).

*Primary Examiner*—Jerome D. Goldberg
*Attorney, Agent, or Firm*—Rose Ann Dabek; Jacobus C. Rasser

[57] ABSTRACT

A pharmaceutical composition for the treatment of cancers or tumors in mammals is disclosed which comprises 2-(2, 4-difluorophenyl)-1,3-bis(1H-1,2,4-triazol-1-yl)propan-2-ol and its derivatives. A chemotherapeutic agent can be used in conjunction with 2-(2,4-difluorophenyl)-1,3-bis(1H-1,2,4-triazol-1-yl)propan-2-ol and its derivatives as can potentiators. 2-(2,4-difluorophenyl)-1,3-bis(1H-1,2,4-triazol-1-yl) propan-2-ol and its derivatives can also be used to treat viral infections, either alone, in conjunction with other anti-viral agents or with a potentiator.

15 Claims, No Drawings

COMPOSITIONS FOR TREATING VIRAL INFECTIONS

TECHNICAL FIELD

This invention is a pharmaceutical composition that is useful for the treatment of cancers and tumors, particularly in human and warm blooded animals containing 2-(2,4-difluorophenyl)-1,3-bis(1H-1,2,4-triazol-1-yl)propan-2-ol and its derivatives. It can be used in combination with other chemotherapeutic agents and potentiators. The same composition can be used to treat viral infections.

BACKGROUND OF THE INVENTION

Cancers, including leukemia, are the leading cause of death in animals and humans. The exact cause of leukemia is not known, but links between certain activities such as smoking or exposure to carcinogens and the incidence of certain types of leukemia and tumors has been shown by a number of researchers.

Many types of chemotherapeutic agents have been shown to be effective against cancers, tumors and leukemia, but not all types of cancer and tumor cells respond to these agents. Unfortunately, many of these agents also destroy normal cells. The exact mechanism for the action of these chemotherapeutic agents are not always known.

Despite advances in the field of cancer and leukemia treatments the leading therapies to date are radiation and chemotherapy and bone marrow transplants. Chemotherapeutic approaches are said to fight cancers that are particularly aggressive. Such cytocidal or cytostatic agents work best on cancers with large growth factors, i.e., ones whose cells are rapidly dividing. To date, hormones, in particular estrogen, progesterone and testosterone, and some antibiotics produced by a variety of microbes, alkylating agents, and anti-metabolites form the bulk of therapies available to oncologists. Ideally cytotoxic agents that have specificity for leukemia, cancer and tumor cells while not affecting normal cells would be extremely desirable. Unfortunately, none have been found and instead agents which target especially rapidly dividing cells (both diseased and normal) have been used.

Clearly, the development of materials that would target cancer or leukemia cells due to some unique specificity for them would be a breakthrough. Alternatively, materials that were cytotoxic to leukemia or cancer cells while exerting mild effects on normal cells would be desirable. Therefore, it is an object of this invention to provide a pharmaceutical composition that is effective in treating leukemia with mild or no effects on normal blood cells More specifically, it is an object of this invention to provide a composition comprising a pharmaceutical carrier and a 2-(2,4-difluorophenyl)-1,3-bis(1H-1,2,4-triazol-1-yl)propan-2-ol and its derivatives as defined herein along with a method for treating cancer, leukemia and tumors.

The use of 2-(2,4-difluorophenyl)-1,3-bis(1H-1,2,4-triazol-1-yl)propan-2-ol and its derivatives in combination with other chemotherapeutic agents which are effective in destroying the tumor is a novel method of treatment. 2-(2,4-Difluorophenyl)-1,3-bis(1H-1,2,4-triazol-1-yl)propan-2-ol and its derivatives can also be used to treat viral infections either alone or in the presence of a potentiator.

SUMMARY OF THE INVENTION

A pharmaceutical composition for treatment of mammals, and in particular, warm blooded animals and humans, which are affected by leukemia comprising a pharmaceutical carrier and an effective amount of 2-(2,4-difluorophenyl)-1,3-bis(1H-1,2,4-triazol-1-yl)propan-2-ol (Fluconazole®) and its derivatives. 2-(2,4-Difluorophenyl)-1,3-bis(1H-1,2,4-triazol-1-yl)propan-2-ol has the formula:

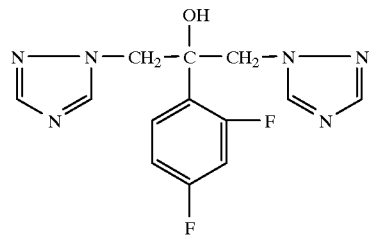

These compositions can be used to inhibit the growth of leukemia, tumors and cancer cells in humans or animals by administration of an effective amount either orally, rectally, topically or parenterally, or intravenously. These compositions do not significantly affect healthy cells.

Potentiators can also be used in combination with 2-(2,4-difluorophenyl)-1,3-bis(1H-1,2,4-triazol-1-yl)propan-2-ol and its derivatives as can chemotherapeutic agents.

These compositions are particularly effective against the influenza virus.

DETAILED DESCRIPTION OF THE INVENTION

A. DEFINITIONS

As used herein, the term "comprising" means various components can be conjointly employed in the pharmaceutical composition of this invention. Accordingly, the terms "consisting essentially of" and "consisting of" are embodied in the term comprising.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will, obviously, vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, a "2-(2,4-difluorophenyl)-1,3-bis(1H-1,2,4-triazol-1-yl)propan-2-ol derivative" includes its esters and ethers and its pharmaceutically acceptable salts.

As used herein, a "pharmaceutical addition salts" are salts of 2-(2,4-difluorophenyl)-1,3-bis(1H-1,2,4-triazol-1-yl)propan-2-ol with an organic or inorganic acid. These preferred acid addition salts are chlorides, bromides, sulfates, nitrates, phosphates, sulfonates, formates, tartrates, maleates, malates, citrates, benzoates, salicylates, ascorbates, and the like.

As used herein, a "pharmaceutical carrier" is a pharmaceutically acceptable solvent, suspending agent or vehicle for delivering the anti-leukemia agent to the animal or human. The carrier may be liquid or solid and is selected with the planned manner of administration in mind.

As used herein, "cancer" or "leukemia" refers to all types of cancers or neoplasm or malignant disease which attack normal healthy blood cells or bone marrow which produces blood cells which are found in mammals.

As used herein, "viruses" includes viruses which cause diseases in warm blooded animals including HIV, influenza, rhinoviruses, herpes and the like.

As used herein, "2-(2,4-difluorophenyl)-1,3-bis(1H-1,2,4-triazol-1-yl)propan-2-ol and its derivatives" includes esters and ethers as well as addition salts.

As used herein "potentiators" are materials such as triprolidine and its cis-isomer or 1H-Benzimidazole-2-propanoic acid which are used in combination with 2-(2,4-difluorophenyl)-1,3-bis(1H-1,2,4-triazol-1-yl)propan-2-ol and its derivatives. Potentiators can affect the immune system or enhance the effectiveness of the drugs.

As used herein "chemotherapeutic agents" includes DNA-interactive Agents, Antimetabolites, Tubulin-Interactive Agents, Hormonal agents and others, such as Asparaginase or hydroxyurea.

B. 2-(2,4-DIFLUOROPHENYL)-1,3-BIS(1H-1,2,4-TRIAZOL-1-YL)PROPAN-2-OL AND ITS DERIVATIVES 2-(2,4-difluorophenyl)-1,3-bis(1H-1,2,4-triazol-1-yl)propan-2-ol and its derivatives has the following structure:

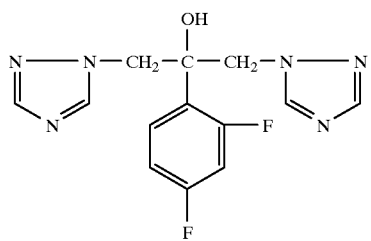

It is prepared according to the method described in U.S. Pat. No. 4,404,216 issued to Richardson (1983).

The derivatives include the lower carboxylic acid esters of the propanol group, for example, acetyl, propanoyl, butyl, pentyl and hexyl esters. Particularly preferred are the esters of carboxylic acids having less than seven carbons, and most preferably propyl esters. Aryl carboxylic acids such as salicylic acid, benzoic acid, and related acids can also be used to esterify the propanol group. Alkyl ethers having less than 7 carbons are also useful derivatives.

The pharmaceutical addition salts are salts of 2-(2,4-difluorophenyl)-1,3-bis(1H-1,2,4-triazol-1-yl)propan-2-ol with an organic or inorganic acid. These preferred acid addition salts are chlorides, bromides, sulfates, nitrates, phosphates, sulfonates, formates, tartrates, maleates, malates, citrates, benzoates, salicylates, ascorbates, and the like.

These compounds are part of a more generic class of fungicides with the formula:

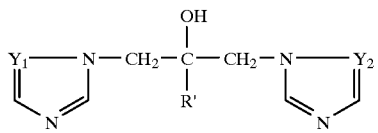

wherein $R^1$ is an optionally-substituted alkyl, cycloalkyl, aryl (2,4-dichlorophenyl) or aralkyl group, and $Y^1$ and $Y^2$ are =CH— or =N—; and salts or metal complexes and ether or esters thereof. While these materials are active against fungus disease, some have been found to be teratogenic. Therefore, those materials which exhibit this property are not useful herein.

C. CHEMOTHERAPEUTIC AGENTS

The chemotherapeutic agents are generally grouped as DNA-interactive Agents, Antimetabolites, Tubulin-Interactive Agents, Hormonal agents and others such as Asparaginase or hydroxyurea. Each of the groups of chemotherapeutic agents can be further divided by type of activity or compound. The chemotherapeutic agents used in combination with 2-(2,4-difluorophenyl)-1,3-bis(1H-1,2,4-triazol-1-yl)propan-2-ol and its derivatives include members of all of these groups. For a detailed discussion of the chemotherapeutic agents and their method of administration, see Dorr, et al, *Cancer Chemotherapy Handbook*, 2d edition, pages 15–34, Appleton & Lange (Connecticut, 1994) herein incorporated by reference.

DNA-Interactive Agents include the alkylating agents, e.g. Cisplatin, Cyclophosphamide, Altretamine; the DNA strand-breakage agents, such as Bleomycin; the intercalating topoisomerase II inhibitors, e.g., Dactinomycin and Doxorubicin); the nonintercalating topoisomerase II inhibitors such as, Etoposide and Teniposde; and the DNA minor groove binder Plcamydin.

The alkylating agents form covalent chemical adducts with cellular DNA, RNA, and protein molecules and with smaller amino acids, glutathione and similar chemicals. Generally, these alkylating agents react with a nucleophilic atom in a cellular constituent, such as an amino, carboxyl, phosphate, sulfhydryl group in nucleic acids, proteins, amino acids, or glutathione. The mechanism and the role of these alkylating agents in cancer therapy is not well understood. Typical alkylating agents include:

Nitrogen mustards, such as Chlorambucil, Cyclophosphamide, Isofamide, Mechlorethamine, Melphalan, Uracil mustard;

Aziridine such as Thiotepa methanesulphonate esters such as Busulfan;

nitroso ureas, such as Carmustine, Lomustine, Streptozocin;

platinum complexes, such as Cisplatin, Carboplatin;

bioreductive alkylator, such as Mitomycin, and Procarbazine, Dacarbazine and Altretamine;

DNA strand breaking agents include Bleomycin;

DNA topoisomerase II inhibitors include the following:

Intercalators, such as Amsacrine, Dactinomycin, Daunorubicin, Doxorubicin, Idarubicin, and Mitoxantrone;

nonintercalators, such as Etoposide and Teniposide.

The DNA minor groove binder is Plicamycin.

The antimetabolites interfere with the production of nucleic acids by one or the other of two major mechanisms. Some of the drugs inhibit production of the deoxyribonucleoside triphosphates that are the immediate precursors for DNA synthesis, thus inhibiting DNA replication. Some of the compounds are sufficiently like purines or pyrimidines to be able to substitute for them in the anabolic nucleotide pathways. These analogs can then be substituted into the DNA and RNA instead of their normal counterparts. The antimetabolites useful herein include:

folate antagonists such as Methotrexate and trimetrexate pyrimidine antagonists, such as Fluorouracil, Fluorodeoxyuridine, CB3717, Azacitidine, Cytarabine, and Floxuridine purine antagonists include Mercaptopurine, 6-Thioguanine, Fludarabine, Pentostatin;

sugar modified analogs include Cyctrabine, Fludarabine; ribonucleotide reductase inhibitors include hydroxyurea.

Tubulin Interactive agents act by binding to specific sites on tubulin, a protein that polymerizes to form cellular microtubules. Microtubules are critical cell structure units. When the interactive agents bind on the protein, the cell can not form microtubules Tubulin Interactive agents include Vincristine and Vinblastine, both alkaloids and Paclitaxel.

Hormonal agents are also useful in the treatment of cancers and tumors. They are used in hormonally susceptible tumors and are usually derived from natural sources. These include:

estrogens, conjugated estrogens and Ethinyl Estradiol and Diethylstilbesterol, Chlortrianisen and Idenestrol;

progestins such as Hydroxyprogesterone caproate, Medroxyprogesterone, and Megestrol;

androgens such as testosterone, testosterone propionate; fluoxymesterone, methyltestosterone;

Adrenal corticosteroids are derived from natural adrenal cortisol or hydrocortisone. They are used because of their anti inflammatory benefits as well as the ability of some to inhibit mitotic divisions and to halt DNA synthesis. These compounds include, Prednisone, Dexamethasone, Methylprednisolone, and Prednisolone.

Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes.

Antihormonal antigens include:

antiestrogenic agents such as Tamosifen, antiandrogen agents such as Flutamide; and antiadrenal agents such as Mitotane and Aminoglutethimide.

Hydroxyurea appears to act primarily through inhibition of the enzyme ribonucleotide reductase.

Asparaginase is an enzyme which converts asparagine to nonfunctional aspartic acid and thus blocks protein synthesis in the tumor.

Taxol is preferred chemotherapeutic agent.

D. POTENTIATORS

The "potentiators" can be any material which improves or increase the efficacy of the pharmaceutical composition or acts on the immune system. One such potentiator is tripro-lidine and its cis-isomer which are used in combination with the chemotherapeutic agents and 2-(2,4-difluorophenyl)-1, 3-bis(1H-1,2,4-triazol-1-yl)propan-2-ol and its derivatives. Triprolidine is described in U.S. Pat. No. 5,114,951 (1992). Another potentiator is procodazole, 1H-Benzimidazole-2-propanoic acid; [β-(2-benzimidazole) propionic acid; 2-(2-carboxyethyl)benzimidazole; propazol]. Procodazole is a non-specific active immunoprotective agent against viral and bacterial infections and can be used with the compositions claimed herein. It is effective with 2-(2,4-difluorophenyl)-1,3-bis(1H-1,2,4-triazol-1-yl)propan-2-ol and its derivatives alone in treating cancers, tumors, leukemia and viral infections or combined with chemotherapeutic agents.

Propionic acid and its salts and esters can also be used in combination with the pharmaceutical compositions claimed herein.

Antioxidant vitamins such as vitamins A, C and E and beta-carotene can be added to these compositions.

E. DOSAGE

Any suitable dosage may be given in the method of the invention. The type of compound and the carrier and the amount will vary widely depending on the species of the warm blooded animal or human, body weight, and the type of cancer or tumor or viral infection being treated. Generally a dosage of between about 1 milligram (mg) per kilogram (kg) of body weight and about 1000 mg per kg of body weight is suitable for either the 2-(2,4-difluorophenyl)-1,3-bis(1H-1,2,4-triazol-1-yl)propan-2-ol and its derivatives or the chemotherapeutic agent. Preferably from 15 mg to about 800 mg/kg of body weight is used. Generally, the dosage in man is lower than for small warm blooded mammals such as mice. A dosage unit may comprise a single compound or mixtures thereof with other compounds or other cancer inhibiting compounds. The dosage unit can also comprise diluents, extenders, carriers, liposomes and the like. The unit may be in solid or gel form such as pills, tablets, capsules and the like or in liquid form suitable for oral, rectal, topical, intravenous injection or parenteral administration or injection into or around the bone marrow. The range and ratio of 2-(2,4-difluorophenyl)-1,3-bis(1H-1,2,4-triazol-1-yl) propan-2-ol and its derivatives to chemotherapeutic agent will depend on the type of cancer or tumor being treated and the particular chemotherapeutic agent.

F. DOSAGE DELIVERY FORMS

The chemotherapeutic agents, 2-(2,4-difluorophenyl)-1, 3-bis(1H-1,2,4-triazol-1-yl)propan-2-ol and its derivatives and, optionally, the potentiators are typically mixed with a pharmaceutically acceptable carrier. This carrier can be a solid or liquid and the type is generally chosen based on the type of administration being used. The active agent can be coadministered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms would also include minerals and other materials to make them compatible with the type of injection or delivery system chosen.

Specific examples of pharmaceutical acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described in the following references: 7 *Modern Pharmaceutics,* Chapters 9 and 10 (Banker & Rhodes, Editors, 1979); Lieberman et al., *Pharmaceutical Dosage Forms: Tablets* (1981); and Ansel, *Introduction to Pharmaceutical Dosage Forms* 2nd Edition (1976).

G. METHOD OF TREATMENT

The method of treatment can be any suitable method which is effective in the treatment of the particular cancer or tumor type being treated. Treatment may be oral, rectal, topical, parenteral or intravenous administration or by injection into the tumor or cancer. The method of applying an effective amount also varies depending on the leukemia, cancer, tumor or virus being treated. It is believed that parenteral treatment by intravenous, subcutaneous, or intramuscular application of the 2-(2,4-difluorophenyl)-1,3-bis (1H-1,2,4-triazol-1-yl)propan-2-ol and its derivatives, formulated with an appropriate carrier, additional cancer inhibiting compound or compounds or diluent to facilitate application will be the preferred method of administering the compounds to warm blooded animals.

In addition to the use of chemotherapeutic agents and potentiators, 2-(2,4-difluorophenyl)-1,3-bis(1H-1,2,4-triazol-1-yl)propan-2-ol and its derivatives can be combined with fungicides, herbicides or other antiviral agents. Preferred herbicides and fungicides include carbendazim, fluoconazole, benomyl, glyphosate and propicodazole.

When the pharmaceutical compositions are used for treatment of viral infection, they can be combined with other anti-viral agents.

ANTIVIRAL EVALUATION WITH HUMAN INFLUENZA VIRUS

Female CD (mice Charles River Breeding Laboratories, Portage, Mich.) 5 to 7 weeks old of age at the time of receipt are used. Mice are approximately 6 to 9 weeks old and weigh approximately 20 to 28 grams at the time test initiation. All mice used in the study do not vary in age by more than 10 days. The mice are housed 6 per cage with bedding. The mice are fed rodent diet 5002 (PMI, St. Louis, Mo.) adlibitum. Fresh water is supplied to the mice adlibitum.

Human influenza virus, strain AT2/Taiwan/1/64 is used to challenge the mice. The organism is stored at approximately −70° C. Prior to infectious challenge a vial of frozen stock is thawed and diluted to the appropriate concentration in buffered saline solution. The mice are anesthetized with Halothane and the virus challenge dose is administered intra-nasally in volume of 50 microliters.

Test materials are administered at the concentration and volume as provided below. On days 1 through 14, 10 mice per group receive the test articles by oral lavage. Saline control animals (10) receive a comparable volume of saline as compared to the test article-dosed mice. Test article dosing is accomplished at approximately 24 hour intervals. On day 0 approximately 4 hours after the second dosing of test articles or saline, all mice are challenged intra-nasally with an infective dose of virus calculated to produce approximately 90% lethality. Animals are observed daily for 21 days after infectious challenge for mortality or moribundity.

| TEST MATERIAL | DOSE (mg/kg) | PERCENT MORTALITY |
|---|---|---|
| Fluconazole | 350 | 0 |
| Fluconazole | 700 | 30% |
| Saline | — | 100% |
| Amantadine | 75 | 0% |

IN VITRO HUMAN COLONY FORMING UNITS TEST

Solid tumors removed from patients are minced into 2 to 5 mm fragments and immediately placed in McCoy's Medium 5A plus 10% heat inactivated newborn calf serum plus 1% penicillin/streptomycin. Within 4 hours, these solid tumors are mechanically disassociated with scissors, forced through No. 100 stainless steel mesh, through 25 gauge needles, and then washed with McCoys medium as described above. Ascitic, pleural, pericardial fluids and bone marrow are obtained by standard techniques. The fluid or marrow is placed in sterile containers containing 10 units of preservative free heparin per ml. of malignant fluid or marrow. After centrifugation at 150×g for 10 minutes, the cells are harvested and washed with McCoy's medium plus 10% heat inactivated calf serum. The viability of cell suspensions is determined on a hemocytometer with trypan blue.

Cells to be cloned are suspended in 0.3% agar in enriched CMRL1066 supplemented with 15% heat inactivated horse serum, penicillin (100 units/ml), streptomycin (2 mg/ml), glutamine (2 mM), insulin (3 units/ml), asparagine (0.6 mg/ml), and HEPES buffer (2 mM). For the continuous exposure test each compound is added to the above mixture. Cells are placed in 35 mm petri dishes in a top layer of agar over an underlayer of agar to prevent growth of fibroblasts. Three plates are prepared for each data point. The plates are placed in a 37° C. incubator, and are removed on day 14 for counting of the number of colonies in each plate. The number of colonies (defined as 50 cells) formed in the 3 compound treated plates is compared to the number of colonies formed in the 3 control plates, and the percent colonies surviving at the concentration of compound can be tabulated. Three positive control plates are used to determine survival rate. Orthosodium vanadate at 200 µg/ml is used as the positive control. If there is <30% cells in the positive control when compared to the untreated control, the test is evaluated.

At concentrations of 0.5 and 5.0 µg/ml in a continuous exposure experiment or single dose experiment Fluconazole was not effective (0/3 and 0/13 respectively) against tumors. At concentration of 50.0 µg/ml in a continuous exposure experiment Fluconazole was effective against lung, non-small cell, and ovarian cancers particularly. Over all 4/13 had ≦50% survival.

What is claimed is:

1. A method of treating viral infections in warm blooded mammals comprising administering a safe and enhanced amount of a member selected from the group consisting of 2-(2,4-difluorophenyl)-1,3-bis(1H-1,2,4-triazol-1-yl) propan-2-ol, its derivatives selected from the group consisting of lower carboxylic acid esters, aryl carboxylic acid esters of alkyl ethers having less than 7 carbon atoms, and mixtures thereof, a safe and effective amount of potentiator, wherein said potentiator increases the effectiveness of said 2-(2,4-difluorophenyl)-1,3-bis(1H-1,2,4-triazol-1-yl) propan-2-ol or its derivatives in the treatment of viral infections.

2. A method according to claim 1 wherein from about 1 mg/kg body weight to about 1000 mg/kg of said 2-(2,4-difluorophenyl)-1,3-bis(1H-1,2,4-triazol-1-yl)propan-2-ol or its derivatives is administered.

3. A method according to claim 1 wherein said 2-(2,4-difluorophenyl)-1,3-bis(1H-1,2,4-triazol-1-yl)propan-2-ol or its derivatives is administered orally or enterically, intravenously, or peritoneally.

4. A method according to claim 1 wherein from about 2 mg/kg body weight to about 1000 mg/kg of said 2-(2,4-difluorophenyl)-1,3-bis(1H-1,2,4-triazol-1-yl)propan-2-ol and its derivatives is administered.

5. A method for treating influenza in warm blooded mammals comprising administering a safe and enhanced amount of a member selected from the group consisting of 2-(2,4-difluorophenyl)-1,3-bis(1H-1,2,4-triazol-1-yl) propan-2-ol, its derivatives selected from the group consisting of lower carboxylic acid esters, aryl carboxylic acid esters of alkyl ethers having less than 7 carbon atoms, and mixtures thereof, a safe and effective amount of potentiator, wherein said potentiator increases the effectiveness of said 2-(2,4-difluorophenyl)-1,3-bis(1H-1,2,4-triazol-1-yl) propan-2-ol or its derivatives in the treatment of viral infections.

6. A method according to claim 5 wherein from about 1 mg/kg body weight to about 1000 mg/kg of said 2-(2,4-difluorophenyl)-1,3-bis(1H-1,2,4-triazol-1-yl)propan-2-ol or its derivatives is administered.

7. A method according to claim 5 wherein said 2-(2,4-difluorophenyl)-1,3-bis(1H-1,2,4-triazol-1-yl)propan-2-ol or its derivatives is administered orally or enterically, intravenously, or peritoneally.

8. A method according to claim 7 wherein from about 2 mg/kg body weight to about 1000 mg/kg of said 2-(2,4-difluorophenyl)-1,3-bis(1H-1,2,4-triazol-1-yl)propan-2-ol and its derivatives is administered.

9. A method of treating viral infections in warm blooded mammals comprising administering a safe and enhanced amount of a member selected from the group consisting of 2-(2,4-difluorophenyl)-1,3-bis(1H-1,2,4-triazol-1-yl)propan-2-ol, its derivatives selected from the group consisting of lower carboxylic acid esters, aryl carboxylic acid esters or alkyl ethers having less than 7 carbon atoms, and mixtures thereof, a safe and effective amount of procodazole, wherein said procodazole increases the effectiveness of said 2-(2,4-difluorophenyl)-1,3-bis(1H-1,2,4-triazol-1-yl)propan-2-ol or its derivatives in the treatment of viral infections.

10. A method according to claim 9 wherein from about 1 mg/kg body weight to about 1000 mg/kg of said 2-(2,4-difluorophenyl)-1,3-bis(1H-1,2,4-triazol-1-yl)propan-2-ol or its derivatives is administered.

11. A method according to claim 10 wherein said 2-(2,4-difluorophenyl)-1,3-bis(1H-1,2,4-triazol-1-yl)propan-2-ol or its derivatives is administered orally or enterically, intravenously, or peritoneally.

12. A method according to claim 11 wherein from about 2 mg/kg body weight to about 1000 mg/kg of said 2-(2,4-difluorophenyl)-1,3-bis(1H-1,2,4-triazol-1-yl)propan-2-ol and its derivatives is administered.

13. A method for treating influenza in warm blooded mammals comprising administering a safe and enhanced amount of a member selected from the group consisting of 2-(2,4-difluorophenyl)-1,3-bis(1H-1,2,4-triazol-1-yl)propan-2-ol, its derivatives selected from the group consisting of lower carboxylic acid esters, aryl carboxylic acid esters or alkyl ethers having less than 7 carbon atoms, and mixtures thereof, a safe and effective amount of procodazole, wherein said procodazole increases the effectiveness of said 2-(2,4-difluorophenyl)-1,3-bis(1H-1,2,4-triazol-1-yl)propan-2-ol or its derivatives in the treatment of viral infections.

14. A method according to claim 13 wherein from about 1 mg/kg body weight to about 1000 mg/kg of said 2-(2,4-difluorophenyl)-1,3-bis(1H-1,2,4-triazol-1-yl)propan-2-ol or its derivatives is administered.

15. A method according to claim 14 wherein said 2-(2,4-difluorophenyl)-1,3-bis(1H-1,2,4-triazol-1-yl)propan-2-ol or its derivatives is administered orally or enterically, intravenously, or peritoneally.

* * * * *